United States Patent [19]

Smith et al.

[11] Patent Number: 4,968,834

[45] Date of Patent: Nov. 6, 1990

[54] RECOVERY OF ACRYLIC ACID AND/OR ETHYL ACRYLATE FROM BLACK ACID

[75] Inventors: Brad L. Smith, Portland; Adolfo Aguilo, Corpus Christi; Cecil D. Homer, Jr., Seabrook, all of Tex.

[73] Assignee: Hoechst Celanese Corporation, Somerville, N.J.

[21] Appl. No.: 521,294

[22] Filed: May 7, 1990

[51] Int. Cl.$^5$ .............................................. C07C 67/48
[52] U.S. Cl. ................................... 560/218; 560/205
[58] Field of Search ........................................ 560/218

[56] References Cited

U.S. PATENT DOCUMENTS

| | | | |
|---|---|---|---|
| 3,067,241 | 12/1962 | Vogt et al. | 560/218 |
| 3,951,756 | 4/1976 | Dirks et al. | 560/218 |
| 4,250,328 | 2/1981 | Fujita et al. | 560/218 |
| 4,301,298 | 11/1981 | Horlenko et al. | 560/218 |
| 4,490,553 | 12/1984 | Chase et al. | 560/218 |

*Primary Examiner*—Paul J. Killos
*Attorney, Agent, or Firm*—Donald R. Cassady

[57] ABSTRACT

Black acid or the sulfuric acid residue obtained in the manufacture of ethyl acrylate by reaction of ethylene and acrylic acid in the presence of sulfuric acid is heated and distilled in a distillation zone in the presence of a solvent to form an overhead mixture comprising an organic phase containing ethyl acrylate and solvent, and an aqueous phase containing water, solvent and acrylic acid. The aqueous phase is recycled to the distillation zone for recovery of additional acrylic acid value from the organic phase.

7 Claims, 1 Drawing Sheet

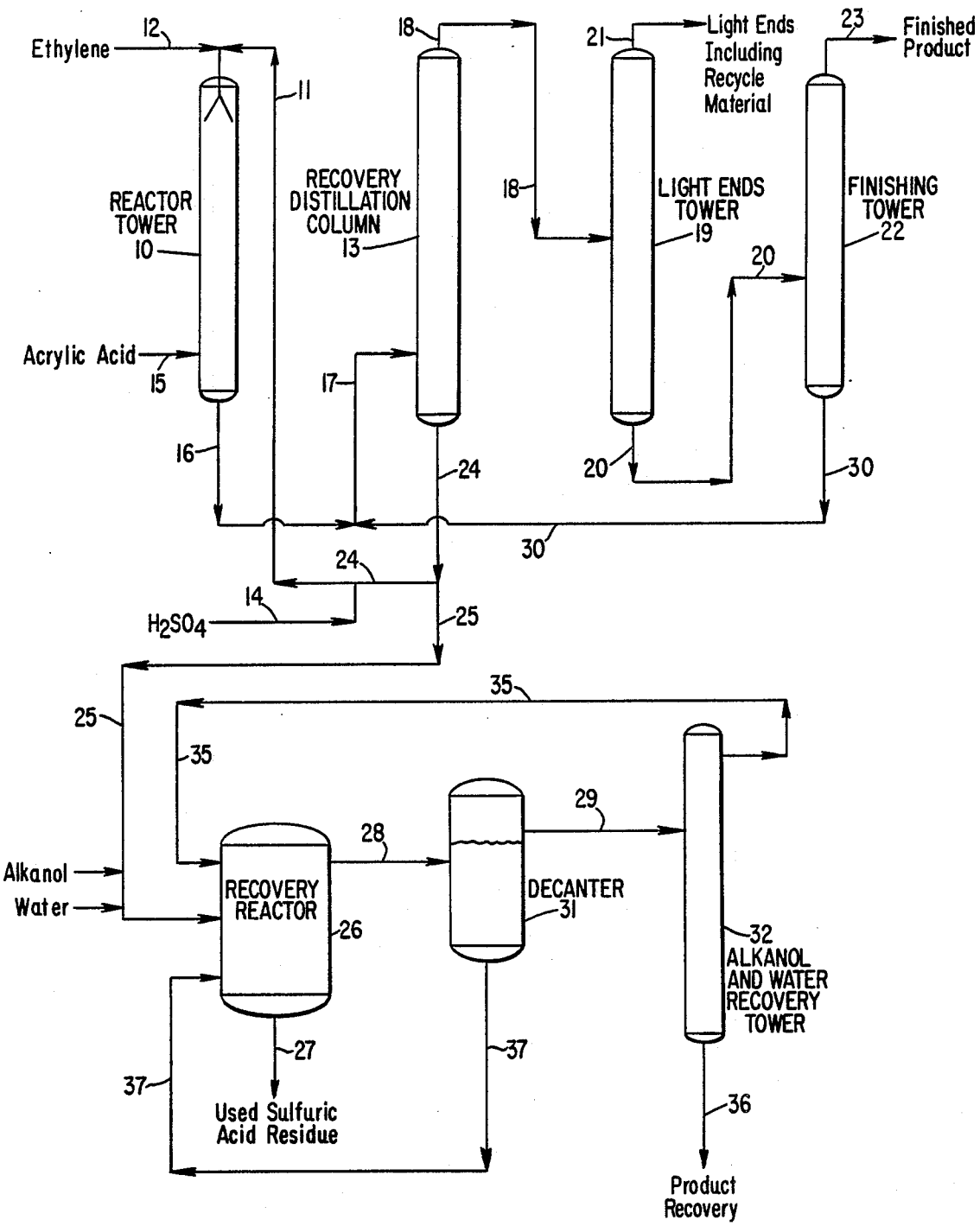

RECOVERY OF ACRYLIC ACID AND/OR ETHYL ACRYLATE FROM BLACK ACID

BACKGROUND OF THE INVENTION

1. Field of the Invention

The present invention relates to a method for recovering lost ethyl acrylate potential (EAP) and, more particularly, to the recovery of acrylic acid and/or ethyl acrylate from spent black acid obtained in the production of ethyl acrylate by reaction of ethylene, acrylic acid and sulfuric acid.

2. Description of the Prior Art

Ethylenically unsaturated organic compounds, such as acrylic acid, methacrylic acid, methacrylic esters, acrylate esters, and the like, are widely used in the production of homopolymers and copolymers. These homopolymers and copolymers, produced readily through the polymerization of the available double bonds of the organic compounds, are widely used in paints, coatings, lacquers, and the like. The olefinic activity of the ethylenically-unsaturated organic compounds makes the polymerized products highly useful for many purposes.

Processes for the production of ethyl acrylate by the interaction of acrylic acid with ethylene in the presence of a sulfuric acid catalyst are well-known. As examples see U.S. Pat. No. 3,703,539, issued Nov. 21, 1972, to DiLiddo; U.S. Pat. No. 3,539,621, issued Nov. 10, 1970, to Cipollone et al; U.S. Pat. No. 3,894,076, issued July 8, 1975, to Van Duyne et al; U.S. Pat. No. 4,490,553, issued Dec. 25, 1984, to Chase et al, and U.S. Pat. No. 3,951,756, issued Apr. 20, 1976, to Dirks et al, all of which are incorporated by reference. In these and other references, the reaction is believed to involve the formation of intermediate sulfates from the reaction of ethylene with sulfuric acid. These sulfates further react with acrylic acid to form ethyl acrylate and product mixtures of unreacted ethylene, acrylic acid, and sulfuric acid residue which must be recycled to the reactor tower. The product mixture is thus sent to a distillation train comprising a recovery distillation tower, a light-ends distillation tower and finishing tower, all of which are conventional. In the recovery tower, the mixture is distilled under vacuum to obtain light-ends of crude ethyl acrylate which are passed to a light-ends distillation column where a partially purified ethyl acrylate bottoms product is sent to a finishing distillation tower for recovery of substantially pure ethyl acrylate. The bottoms product from the recovery distillation tower is a sulfuric acid residue or black acid stream containing free sulfuric acid, ethyl hydrogen sulfate, diethyl sulfate, lactone polyester, acrylic acid, and ethyl acrylate. The sulfuric acid residue or black acid stream is removed as bottoms residue from the recovery distillation tower and then returned to the reactor tower to repeat the cycle. During the ethylene-acrylic acid reaction, black acid builds up in viscosity and to maintain proper viscosity values, which allow favorable use of process equipment and not retard reaction rates, some of the black acid is periodically purged from the system, usually about 1 to 5 wt.%, and new reactants are added. The purged or blow down material, which is rich in ethyl acrylate potential, is reprocessed for sulfur recovery. During the reprocessing of the spend black acid, the ethyl acrylate potential (EAP) is thus lost. Improvement in ethyl acrylate yields would be substantially increased if the EAP could be recovered from the black acid.

SUMMARY OF THE INVENTION

The present invention is directed to the recovery of ethyl acrylate potential from spent black acid by forming a mixture of black acid with a solvent selected from the group of water, a lower alkanol of 1 to 4 carbon atoms, or mixtures thereof, heating and distilling the mixture to obtain an overhead product mixture consisting of an organic phase containing mostly ethyl acrylate and ethanol, and an aqueous phase which is mostly water but contains ethanol and acrylic acid. The aqueous phase is thereafter recycled to the heating and distillation step for further recovery of lost ethyl acrylate potential (EAP).

DESCRIPTION OF THE INVENTION

In carrying out the method of the invention, black acid as obtained in the conventional manufacture of ethyl acrylate by reaction of ethylene, acrylic acid, and sulfuric acid is mixed with a solvent such as water, a lower alkanol, or a mixture thereof, and then heated and distilled at temperatures within the range of about 50° C. to 250° C., preferably about 120° C. to 170° C., to vaporize ethyl acrylate and acrylic acid and provide an overhead product mixture which consists of two phases, an organic phase comprising ethyl acrylate and ethanol, and an aqueous phase comprising water, ethanol, and acrylic acid. The aqueous phase is recycled to the heating and distillation step for further recovery of ethyl acrylate potential (EAP) as more fully described hereinafter. The organic phase may also be recycled to the distillation step if desired.

While the chemistry of the many and complex reactions which occur during the manufacture of ethyl acrylate is not fully understood, experiments and observations allow some of the following postulations:

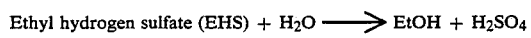

(1) Ethyl hydrogen sulfate (EHS) + H$_2$O ⟶ EtOH + H$_2$SO$_4$

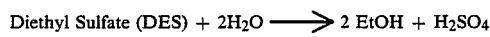

(2) Diethyl Sulfate (DES) + 2H$_2$O ⟶ 2 EtOH + H$_2$SO$_4$

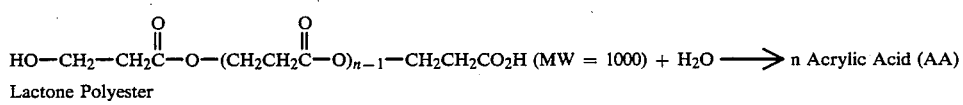

(3) HO—CH$_2$—CH$_2$C(=O)—O—(CH$_2$CH$_2$C(=O)—O)$_{n-1}$—CH$_2$CH$_2$CO$_2$H (MW = 1000) + H$_2$O ⟶ n Acrylic Acid (AA)

Lactone Polyester

Allowing the following reaction to proceed:

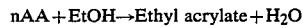

nAA + EtOH → Ethyl acrylate + H$_2$O

Additional ethanol may be added if insufficient EtOH is not generated by reactions (1) and (2). Again, while the mechanism of the present invention is not clearly understood, it is believed that the sulfuric acid in the black acid stream becomes attached to acrylic acid, and to some degree ethyl acrylate, through hydrogen bonding.

Since water in the system is removed in the recovery distillation tower, the sulfuric acid becomes even more strongly attached to acrylic acid which, in fact, acts as a base. However, when a solvent such as water, a lower alkanol, or mixtures thereof, is subsequently added to the black acid stream, it frees acrylic acid and ethyl acrylate and thereby permits their recovery by simple distillation and phase separation of the resulting organic and aqueous phases. In the absence of water or the alkanol solvent, high temperatures are ineffective for separating the sulfuric acid residue or black acid stream from ethyl acrylate and acrylic acid.

The heating and distillation step of the black acid-solvent mixture can be conducted at atmospheric pressure or the pressure may be reduced or increased above atmospheric at temperatures ranging from about 100° C. to 170° C. In general, the pressure will range from 50 mm Hg absolute up to about 3 atmospheres, preferably about 1 atmosphere. The distillation can be conducted in a batch, continuous, or semi-continuous operation. The time of distillation will vary depending on the temperature and pressure variables, however, it generally has been found that in batch type operations employing a stirred reactor good rates of reaction are obtained within six hours or less.

The solvent used in accordance with the invention is water or a lower alkanol of 1 to 4 carbon atoms, such as methanol, ethanol, propanol or butanol, or an aqueous mixture of the alkanol containing 0 to 100% by weight of water, preferably about 60 to 85% by weight of water. The volume of solvent per volume of black acid charged to the heating and distillation zone will depend on the concentration of sulfuric acid and heavy ends (metal salts of dibasic acids) in the black acid residue stream. Typically, approximately 40 to 50 wt. % of the black acid residue is ethyl acrylate potential (EAP) material comprising acrylic acid, ethyl acrylate, ethanol, ethyl hydrogen sulfate, and some diethyl sulfate, whereas about 40 wt. % of the stream is sulfuric acid (determined as wt. % sulfur) and about 10 wt. % is the very heavy ends material. Accordingly, the volume ratio of solvent to feedstock will generally vary within the range of from about 1 to 1 to about 30 to 1 or higher, the preferred solvent to feedstock ratios being determined generally by selection and trial in accordance with well known engineering procedures therefor.

The over-all process of the present invention is schematically represented in the drawing in which a combination of substantially anhydrous sulfuric acid medium supplied through line 11 and ethylene supplied through line 12 is sprayed into reactor tower 10 and mixed. The sulfuric acid medium is comprised of sulfuric acid residue o bottoms from the product recovery distillation tower 13 along with make-up sulfuric acid added through line 14. The sulfuric acid residue (referred to in the industry as "black acid") recovered from the recovery distillation tower 13 is a mixture of various compounds and contains sulfuric acid, intermediate sulfates from the reaction of ethylene and sulfuric acid, unreacted acrylic acid, some small amounts of ethyl acrylate, and various other compounds.

In the reactor tower 10, the main reaction of concern is the liquid-phase reaction of ethylene-enriched liquid with sulfuric acid to give various intermediate sulfate salts, such as ethyl hydrogen sulfate and diethyl sulfate, which will then further react with acrylic acid, supplied through line 15, to form ethyl acrylate. Adequate mixing of the reaction mixture in the reaction tower 10 can be obtained by mechanical stirring or recycle of the reaction products. (Neither mixing techniques are shown in the drawing). The reactants' residence time in the reactor tower 10 must be sufficient to obtain substantially (preferably at least a 90% completion) complete reaction of ethylene and acrylic acid. Temperatures in the reaction tower should be maintained within the range of about 100° C. to about 150° C., preferably 110° C. to 130° C. and the pressure should be maintained within the range of about 100 to about 300 psig, preferably 130 to 200 psig.

The reaction products from the reactor tower 10 are withdrawn through line 16 and passed through a pressure reduction valve (not shown) and thence to the recovery distillation tower 13. The distillation section of the recovery distillation tower may be of conventional design, and may contain packing, sieve type trays or dual flow trays. The distillation section should contain an equivalent of at least four theoretical trays. A vacuum is maintained in the recovery distillation tower 13 by conventional means so that the pressure is less than about 200 mm of mercury absolute, and preferably within the range of 20 to 150 mm of mercury absolute. The still-pot temperature should be maintained within the range of about 100° C. to about 170° C., preferably 110° C. to 130° C., and the still-head temperature within the range of about 28° C. to about 45° C., preferably 30° C. to 40° C.

The feed line 17 to the recovery distillation tower 13 is directed preferably to the lower third, and more preferably to the base of the tower. In the recovery distillation tower 13, the light-ends of crude ethyl acrylate, comprising mainly ethyl acrylate, small amounts of unreacted ethylene, and other uncondensables, are removed overhead through line 18 and passed to the light-ends distillation tower 19 (of conventional distillation design). Partially purified ethyl acrylate product is removed as bottoms through line 20. A stream comprising mainly unreacted ethylene is removed from the light ends distillation tower 19 through line 21 and may be disposed of or recycled (not shown) to the reactor tower 10 as desired. If recycled, a scrubbing to remove sulfur oxides is recommended. As pointed out above, operation according to the present invention generally results in a very small amount of unreacted ethylene such that the amounts of ethylene removed through line 21 will be relatively small. The partially purified ethyl acrylate product recovered through line 20 is further treated by fractionation in the finishing distillation tower 22 to obtain, through line 23, a substantially pure ethyl acrylate having a purity greater than 95 percent, preferably about 99.9 percent or higher.

The ethyl acrylate product residue of the finishing distillation tower 22 is removed through line 30 and can be passed through line 30 into line 17 which is combined with the reaction products passed into the recovery distillation tower 13 from line 16. If all of the ethyl acrylate product residue from the finishing distillation tower is recycled to the recovery distillation tower 13, the result can be a greater degree of fouling in the recovery distillation tower caused by black acid viscosity increase and a subsequent loss of product polymer. Passing a portion of the ethyl acrylate product residue of the finishing distillation tower to recovery reactor 26 is preferred since process efficiency is obtained whereby fouling of the recovery distillation tower is decreased with less polymer being formed.

In operating the recovery distillation tower 13, the residence time of the reaction products in the base of the tower should be as low as possible because at temperatures required in the reboiler for vaporization some polymerization may occur. It is desirable to have a feed stream lean in acrylic acid being fed to the recovery distillation tower since this will result in less polymer formation.

Although not shown on the drawing, the addition of a polymerization inhibitor is generally desirable when producing or purifying ethyl acrylate. Such inhibitors are known, and can be materials absolute in the reaction medium or soluble in the product obtained from the recovery distillation tower. Suitable polymerization inhibitors include hydroquinone, phenothiazine, the methyl ether of hydroquinone, quinone and the like. The polymerization inhibitor can be introduced to the reaction vessel in the used sulfuric acid residue or through any other convenient part of the system. The inhibitor is preferably added to lines 18, 21, 23 and 25. The inhibitor can be added in line 18 from which it is carried out through to the light ends distillation tower 19, then into the finishing distillation tower 22 and into the residue of the finishing distillation tower 22. It may be also added to line 29 where it passes into the alkanol recovery tower.

The sulfuric acid residue or black acid stream referred to above, containing sulfuric acid, intermediate sulfates, unreacted acrylic acid and the like is removed as bottoms residue from the recovery distillation tower 13 through line 24. A blowdown of a minor portion of the bottoms stream or sulfuric acid residue which is approximately 1 to 5 percent by weight of the total sulfuric acid residue is taken by means of line 25 so as to prevent the buildup of impurities in the system and is sent to recovery reactor 26. The remaining major portion of the sulfuric acid residue can be recycled via line 24 through line 11 to the reactor tower 10 in combination with ethylene introduced via line 12.

The sulfuric acid residue is passed through line 25 along with water and alkanol solvent to recovery reactor 26 which is heated to a temperature of 100° C. to about 170° C., preferably about 130° C. to 160° C., to flash overhead a stream containing ethyl ether, alkanol, ethyl acrylate, acrylic acid and water. The overhead stream is passed through line 28 to decanter 31 for separation into two phases, an organic top phase which is mostly ethyl acrylate, alkanol and acrylic acid, and an aqueous bottom phase which is mostly water but contains some alkanol and ethyl acrylate potential (acrylic acid and/or ethyl acrylate) depending upon the amount of alkanol charged. In decanter 31 the organic phase is passed via line 29 to the alkanol and water recovery tower 32 where alkanol, ethyl acrylate and small amounts of water and ethyl ether are distilled and removed overhead for recycle to recovery reactor 26. Recovery tower 32 serves as an alkanol stripping column and is operated at temperatures of 70° C. to 110° C., preferably about 80° C. to 95° C., using a reflux ratio of 10:1 preferably about 3:1, or no reflux at all depending upon the number of trays in the column. By recycling the overhead of recovery tower 32 back to reactor 26 a savings in make-up alkanol and water is obtained. Although not completely understood at this time, it is believed that ethyl ether decomposes under the reaction conditions in reactor 26 and reacts as ethanol does to form ethyl acrylate, thus providing additional savings in ethanol.

The aqueous or bottom phase from decanter 31 is recycled through line 37 to recovery reactor 26. The aqueous phase contains mainly water and alkanol along with lesser amounts of ethyl ether, ethyl acrylate and acrylic acid. Recycle of aqueous stream 37 is an important feature of the invention since less make-up water and ethanol are needed for reactor 26; further, since there is at least as much acrylic acid in the aqueous phase as there is in the organic phase, recycle of the aqueous phase via line 37 will force acrylic acid into the organic phase by conversion of the same to ethyl acrylate, which thus saves the cost of a high-energy, water-/acrylic acid separation step. To illustrate the process of this invention, referring to the description of the drawing and using the conditions as described, 3055 pounds per hour of ethylene and 7850 pounds per hour of acrylic acid are added to the reactor tower 10 into which 92,967 pounds per hour of sulfuric acid medium is recycled with 879 pounds per hour of anhydrous sulfuric acid makeup is added. From the recovery distillation tower 13, 14,199 pounds per hour of crude ethyl acrylate product are obtained overhead through line 18. From the bottom of the recovery distillation tower 13, 2789 pounds per hour of sulfuric acid residue are removed from the recycle sulfuric acid medium and passed through line 25 along with 169 pounds of ethanol and 728 pounds of water per hour to recovery reactor 26 at a rate of 3686 pounds per hour. 14,199 Pounds per hour of crude ethyl acrylate product is passed through line 18 to the light-ends distillation tower 19. 157 Pounds per hour of light-ends are recovered in the overhead line 21 and 13,962 pounds per hour of partially purified ethyl acrylate product is passed through line 20 to the finishing distillation tower 22. 9380 Pounds per hour of purified ethyl acrylate are recovered through line 23 and 4582 pounds per hour of ethyl acrylate product residue are recovered and passed through lines 30 and 17 to distillation column 13.

Recovery reactor 26 is heated to about 145° C. to distill overhead, 101 pounds of ethyl ether, 956 pounds ethanol, 931 pounds ethyl acrylate, 451 pounds acrylic acid and 2581 pounds of water which are passed through line 28 to decanter 31. The organic phase, comprising 69 pounds of ethyl ether, 205 pounds ethanol, 749 pounds ethyl acrylate, 201 pounds acrylic acid and 174 pounds of water, a total of 1398 pounds per hour, is sent via line 29 to the alkanol and water recovery tower 32 to strip out the ethanol from the organic phase and allow it to be recycled back to reactor 26 via line 35. Recycle stream 35 contains 41 pounds of ethyl ether, 260 pounds ethanol, 345 pounds ethyl acrylate and 33 pounds of water which are recycled tower 32 via line 36 comprises 64 pounds ethanol, 365 pounds ethyl acrylate, 271 pounds acrylic acid and 100 pounds water which are removed at a rate of 800 pounds per hour. The aqueous stream is removed form decanter 31 via line 37 and is recycled to reactor 26. This stream contains 33 pounds diethyl ether, 750 pounds ethanol, 182 pounds ethyl acrylate, 240 pounds acrylic acid and 2408 pounds of water and is recycled at a rate of 3613 pounds per hour.

The following examples illustrate the best mode now contemplated for carrying out the invention.

The following examples demonstrate the efficiency improvement by recycling the aqueous phase to recover the contained acrylic value. Example 1 is without recycle of aqueous phase, Example 2 is with recycle.

EXAMPLE 1

In a hood, a reactor was set up which consisted of a three-necked, 1-L round-bottom flask with mechanical stirrer, thermal well for thermometer, and a Dean-Stark trap with attached condenser to collect the distillate. At the base of the glass vessel was a stopcock through which black acid feed could be added. In a separate flask, the black acid, water, and ethanol were well mixed and placed in a 1-L, graduated, glass vessel (buret). The black acid mixture in the feed vessel was stirred by mechanical stirrer to insure homogeneity. The black acid mixture was added to the reactor via a lab pump of which the feed rate was controlled by the temperature in the reactor. A side arm was glass-blown into the side of the reactor flask so that a periodic blowdown could be taken in order to control the reactor level. The reactor was heated with a slitted mantle (slitted so the stopcock at the bottom of the reactor could fit through). An additional slitted mantle was placed over the upper part of the flask to provide additional heat. Also, the Dean-Stark trap was heat-traced up to the condenser to prevent the liquid from condensing back into the reactor. The reactor was charged with about 500 grams of black acid, the stirrer begun and then the reactor was heated to 145° C. Once the temperature was reached, the black acid mixture from the feed vessel containing 16.5% ethanol, 39.5% black acid and 44% water was pumped into the reactor at such a rate as to maintain the reactor solution at 145° C. A blowdown was taken periodically to maintain a constant level in the reactor. The liquid overhead (which consisted of two phases) was collected via the Dean-Stark trap and analyzed by GC. Upon start-up the system was allowed to equilibrate (maintain constant temperature and composition in the reactor pot) before the overhead product was saved and analyzed (4–8 hrs). The overhead product was then collected over a least a two hour period. The overhead phases were separated and analyzed for acrylic acid and ethyl acrylate content. In this manner a total of 146.6 g of black acid, 61.9 g of ethanol, and 164.5 g of water were fed. Analysis of the overhead is given below in Table 1.

TABLE I

| PHASE | wt grams | ethyl acrylate grams/moles | acrylic acid, grams/moles | water grams | ethanol grams |
|---|---|---|---|---|---|
| Organic | 54.5 | 30.1/0.30 | 4.8/0.067 | 5.7 | 10.0 |
| Aqueous | 185.5 | 6.9/0.069 | 5.6/0.078 | 131.0 | 42.0 | moles of Acrylic value in Organic phase = 0.367
moles of Acrylic value in feed black acid = 0.55
% Yield = 0.367/0.55 × 100 = 67%

Thus, only 67% of the possible acrylic acid value was recovered without some method for recovering acrylic acid value from the aqueous phase.

The acrylic value (acrylic acid+ethyl acrylate) must be removed from the water of the aqueous phase before it can be added to the ethyl acrylate unit. This would require some kind of extraction or distillation step. By recycling the aqueous phase to the recovery reactor as shown in example 2 the acrylic value is forced into the organic phase which can be added to the ethyl acrylate unit without further purification.

EXAMPLE 2

For example 2 we used the same equipment as described in example 1, as well as the same procedure except that, for this example, all of the aqueous phase was mixed with the feed black acid (thus recycling the aqueous phase). Supplemental ethanol and water were added to the black acid and aqueous phase mixture in order to get a feed solution containing approximately 16.5% ethanol, 44% water and 39.5% black acid. Therefore, in this manner 4653 g of black acid, 898 g supplemental ethanol, and 844 g supplemental water were fed. Analysis of the organic phase is given below:

| Phase | wt grams | ethyl acrylate grams/moles | acrylic acid, grams/moles | water grams | ethanol grams |
|---|---|---|---|---|---|
| Organic | 2218 | 1275/12.8 | 282/3.9 | 211 | 364 | moles of Acrylic value in Organic phase = 16.7
moles of Acrylic value in feed black acid = 18.6
% Yield = 16.7/18.6 × 100 = 90%

By recycling the aqueous phase there is no need for further equipment to separate the acrylic value from the water phase. An increase in yield of from 67% to 90% by recycling the aqueous phase was obtained.

What is claimed is:

1. In a method for producing ethyl acrylate by reacting ethylene and acrylic acid in the presence of sulfuric acid to obtain ethyl acrylate and a sulfuric acid residue containing sulfuric acid, ethyl hydrogen sulfate, diethyl sulfate, acrylic acid, ethyl acrylate, polyesters of acrylic acid and lactone polymers, wherein a first mixture of said sulfuric acid residue is formed with a solvent selected from the group consisting of water, a lower alkanol having 1 to 4 carbon atoms, or an aqueous mixture of said alkanol, and wherein said first mixture is heated and distilled in a distillation zone at temperatures within the range of about 50° C. to 250° C. at pressures of about 30 mm Hg absolute up to 3 atmospheres to vaporize acrylic acid and ethyl acrylate and form an overhead mixture comprising an organic phase containing ethyl acrylate and ethanol and an aqueous phase containing water, ethanol and acrylic acid, the improvement comprising recycling the aqueous phase to said distillation zone, and thereafter recovering additional acrylic acid value from the organic phase.

2. The method of claim 1 wherein the heating and distillation is carried out at temperatures of about 120° C. to 170° C. at a pressure of about 1 atmosphere.

3. The method of claim 1 wherein the solvent is water.

4. The method of claim 1 wherein the solvent is a lower alkanol having 1 to 4 carbon atoms.

5. The method of claim 1 wherein the solvent is an aqueous mixture of said alkanol containing from 0 to 100 wt.%

6. The method of claim 1 wherein the solvent is an aqueous mixture of said alkanol containing about 60 to 85 wt.%

7. The method of claim 5 wherein the alkanol is ethanol.

* * * * *